(12) United States Patent
Salahieh

(10) Patent No.: US 8,048,103 B2
(45) Date of Patent: Nov. 1, 2011

(54) FLATTENED TIP FILTER WIRE DESIGN

(75) Inventor: Amr Salahieh, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1486 days.

(21) Appl. No.: 10/702,279

(22) Filed: Nov. 6, 2003

(65) Prior Publication Data
US 2005/0101987 A1    May 12, 2005

(51) Int. Cl.
*A61M 29/00* (2006.01)
(52) U.S. Cl. .................................... 606/200; 604/96.01
(58) Field of Classification Search .................. 606/159, 606/191, 194, 200, 198; 604/96.01
See application file for complete search history.

(56) References Cited

U.S. PATENT DOCUMENTS

| | | | |
|---|---|---|---|
| 5,152,777 A | 10/1992 | Goldberg et al. | |
| 5,695,519 A | 12/1997 | Summers et al. | |
| 5,709,704 A | 1/1998 | Nott et al. | |
| 5,769,816 A | 6/1998 | Barbut et al. | |
| 5,814,064 A | 9/1998 | Daniel et al. | |
| 5,827,324 A | 10/1998 | Cassell et al. | |
| 5,876,367 A | 3/1999 | Kaganov et al. | |
| 5,895,399 A | 4/1999 | Barbut et al. | |
| 5,911,734 A | 6/1999 | Tsugita et al. | |
| 6,001,118 A | 12/1999 | Daniel et al. | |
| 6,129,739 A * | 10/2000 | Khosravi ............... | 606/200 |
| 6,152,946 A * | 11/2000 | Broome et al. ......... | 606/200 |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,277,138 B1 | 8/2001 | Levinson et al. | |
| 6,277,139 B1 * | 8/2001 | Levinson et al. ....... | 606/200 |
| 6,371,971 B1 | 4/2002 | Tsugita et al. | |
| 6,540,722 B1 | 4/2003 | Boyle et al. | |
| 6,544,279 B1 * | 4/2003 | Hopkins et al. ........ | 606/200 |
| 6,569,184 B2 | 5/2003 | Huter | |
| 6,575,996 B1 | 6/2003 | Denison et al. | |
| 6,589,263 B1 * | 7/2003 | Hopkins et al. ........ | 606/200 |
| 6,602,271 B2 | 8/2003 | Adams et al. | |
| 6,605,102 B1 | 8/2003 | Mazzochi et al. | |
| 6,610,077 B1 * | 8/2003 | Hancock et al. ....... | 606/200 |
| 6,616,682 B2 | 9/2003 | Joergensen et al. | |
| 6,620,182 B1 | 9/2003 | Khosravi et al. | |
| 6,635,070 B2 | 10/2003 | Leeflang et al. | |
| 2002/0022858 A1 * | 2/2002 | Demond et al. ........ | 606/200 |
| 2002/0091408 A1 * | 7/2002 | Sutton et al. .......... | 606/200 |
| 2002/0095171 A1 | 7/2002 | Belef | |
| 2002/0183783 A1 | 12/2002 | Shadduck | |
| 2003/0004539 A1 | 1/2003 | Linder et al. | |
| 2003/0078519 A1 | 4/2003 | Salahieh et al. | |
| 2003/0144689 A1 * | 7/2003 | Brady et al. ........... | 606/200 |
| 2003/0163064 A1 | 8/2003 | Vrba et al. | |
| 2003/0171770 A1 | 9/2003 | Kusleika et al. | |
| 2003/0191493 A1 | 10/2003 | Epstein et al. | |
| 2003/0208224 A1 | 11/2003 | Broome | |

FOREIGN PATENT DOCUMENTS

| | | |
|---|---|---|
| WO | WO 01/72205 A2 | 10/2001 |
| WO | WO 03/055413 A2 | 7/2003 |

* cited by examiner

*Primary Examiner* — Victor Nguyen
(74) *Attorney, Agent, or Firm* — Seager, Tufte & Wickhem LLC

(57) ABSTRACT

An embolic protection filtering device having an improved filter loop and methods of making and using the same. The filter loop may include a coil or coil region and a flattened region. Additionally, the filter loop may include a loop tip.

15 Claims, 4 Drawing Sheets

FLATTENED TIP FILTER WIRE DESIGN

FIELD OF THE INVENTION

The present invention pertains to embolic protection filtering devices. More particularly, the present invention pertains to filters having an improved filter wire loop.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The present invention pertains to embolic protection filtering devices. In at least some embodiments, an embolic protection filtering device includes a filter coupled to a shaft or filter cartridge. The filter may include a filter loop and a filter membrane coupled to the filter loop. The filter loop may include a coil and a flattened region. These and other structural features and characteristics are described in more detail below.

DETAILED DESCRIPTION

Figure 1:
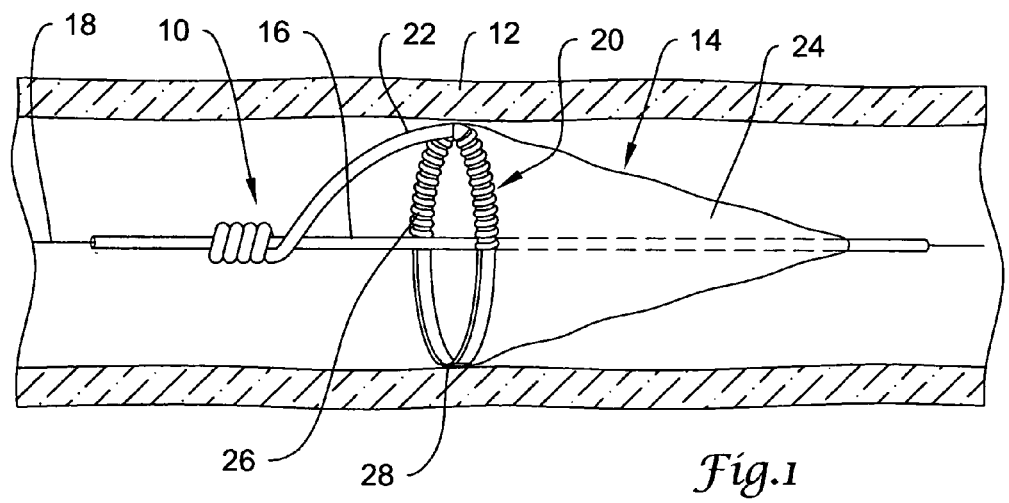
FIG. 1 is a partial cross-sectional plan view of an example embolic protection filtering device disposed in a blood vessel.

The following description should be read with reference to the drawings wherein like reference numerals indicate like elements throughout the several views. The detailed description and drawings illustrate example embodiments of the claimed invention.

An example embolic protection filtering device 10, disposed in a blood vessel 12, is illustrated in FIG. 1. Device 10 may include an embolic protection filter 14 coupled to a shaft or filter cartridge 16. In at least some embodiments, cartridge 16 may be configured to be slidable along a medical device, for example, a guidewire 18. Filter 14 may include a filter loop 20 and one or more struts 22 extending between loop 20 and cartridge 16. A filter membrane 24 may be coupled to filter loop 20 and, for example, extend distally therefrom.

In at least some embodiments, filter loop 20 may include a coil 26. Coil 26 may be manufactured from any appropriate material and may, for example, include a radiopaque material. Radiopaque materials are understood to be materials capable of producing a relatively bright image on a fluoroscopy screen or another imaging technique during a medical procedure. This relatively bright image aids the user of device 10 in determining the location of loop 20. Some examples of radiopaque materials can include, but are not limited to, gold, platinum, palladium, tantalum, tungsten alloy, plastic material loaded with a radiopaque filler, and the like. In some embodiments, coil 26 may be defined by one or more radiopaque wires or fibers wound about a portion of filter loop 20. Alternatively, coil 26 may be defined by helical windings formed in filter loop 20 (as described below in relation to FIG. 5). Some of the details, features, and characteristics of coil 26 and are described in more detail below.

Figure 2:
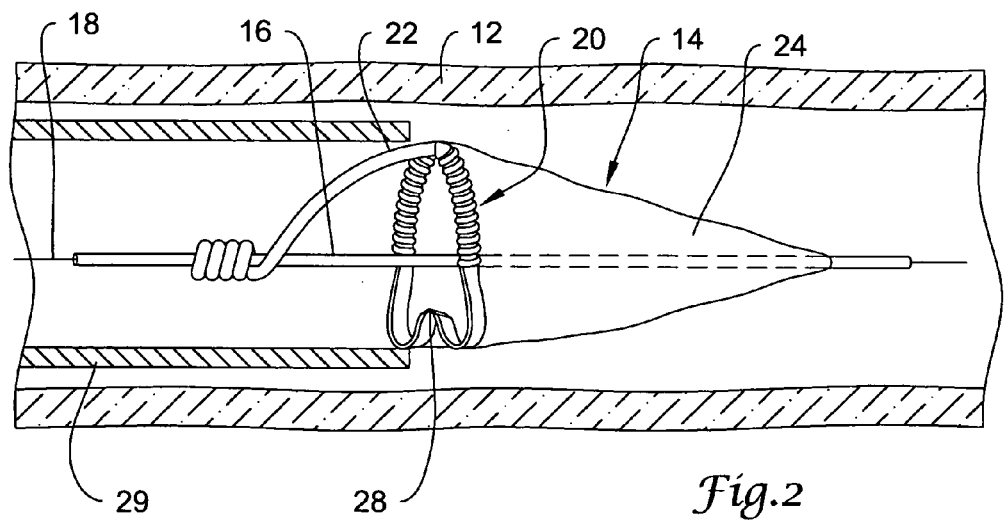
FIG. 2 is a partial cross-sectional plan view of an example embolic protection filtering device and a sheath disposed in a blood vessel.

Filter loop 20 may also include a loop tip 28. Loop tip 28 may be defined by a thinned ribbon or otherwise differentiated portion of filter loop 20. In at least some embodiments, loop tip 28 may define a region of filter loop 20 where filter 14 (and filter loop 20) may fold or otherwise define a predictable position for filter 14 to fold. For example, FIG. 2 illustrates filter 14 folded at loop tip 28 and disposed in a retrieval and/or delivery sheath 29. Some of the details, features, and characteristics of loop tip 28 are described in more detail below.

As stated above, filter 14 may be coupled to shaft or filter cartridge 16 that may be tubular so as to be slidable over guidewire 18 or other medical devices. It can be appreciated, however, that shaft or cartridge 16 is not intended to be limited to tubes that are slidable over guidewires. For example, shaft or cartridge 16 may also be a solid shaft, guidewire, catheter (e.g., therapeutic, diagnostic, or guide catheter), endoscopic device, laproscopic device, and the like, or any suitable device.

It can be seen in FIG. 1, that in at least some embodiments the one or more struts 22 may be coupled to cartridge 16. For example, struts 22 may be coupled to cartridge 16 by helically wrapping them about cartridge 16. Alternatively, struts 22 may be coupled to cartridge 16 using a suitable mechanical connector or coupling such as a crimp connector. Other coupling methods may also be used such as welding (e.g., resistance or laser welding), soldering, brazing, adhesive, or the like, or combinations thereof.

In general, filter 14 may be adapted to operate between a first generally collapsed configuration and a second generally expanded configuration for collecting debris in a body lumen. In some embodiments, filter 14 can be delivered to an appropriate intravascular location, for example "downstream" of an intravascular lesion, using an appropriate filter delivery and/or retrieval device (e.g., sheath 29). Similarly, filter 12 can be removed from the vasculature at the desired time with device 18 or another suitable device (e.g., sheath 29).

Figure 3:
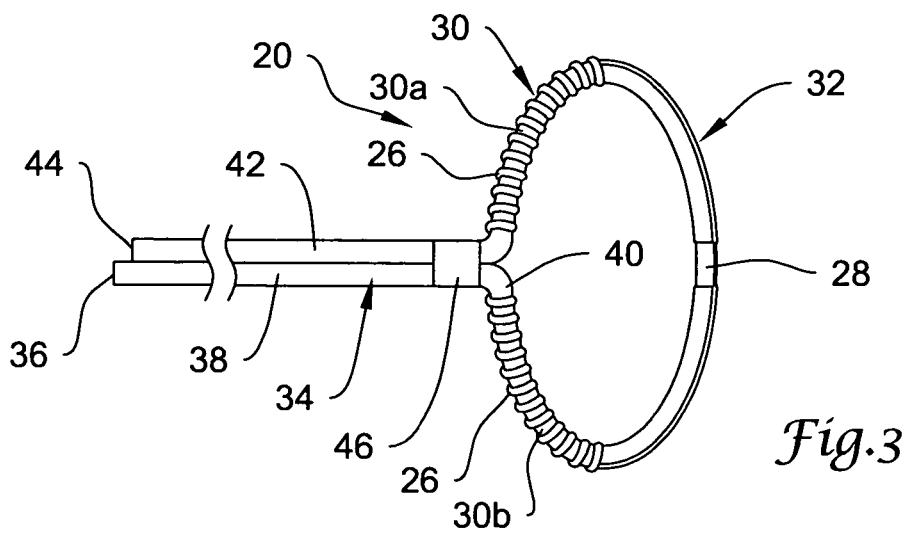
FIG. 3 is a plan view of an example filter loop.

An enlarged view of filter loop 20, with filter membrane 24 removed therefrom, is shown in FIG. 3. Filter loop 20 may be manufactured from any appropriate material such as metals, metal alloys, polymers, composite materials, and the like. Some examples of suitable metals and metal alloys include stainless steel, such as 304v stainless steel; nickel-titanium or other shape memory alloys, such as nitinol, nickel-chromium alloy, nickel-chromium-iron alloy, cobalt alloy, or the like; or other suitable material. In embodiments where filter loop 20 includes a shape-memory alloy, loop 20 can be manufactured self-expanding. According to this embodiment, loop 20 may be set so that when filter loop 20 is unconstrained and disposed at an appropriate location (and thermal condition), it can resort to predefined shape, for example, and expand filter 14.

Filter loop 20 may include multiple sections including, for example, a first section 30 and a second section 32. In some embodiments, first section 30 is generally rounded and, thus, has a generally circular cross-sectional shape. Second section 32 may define an alternative shape or configuration that differs from first section 30. For example, second section 32 may be flattened relative to first section 30 so as to have a somewhat squared or rectangular cross-sectional shape. Second section 32 may be flattened using any appropriate manufacturing technique, for example known stamping techniques, coining techniques, other mechanical machining, and the like. Of course, the exact shapes of first section 30 and second section 32 are not intended to be limited to what is described above as they may be any appropriate shape.

In addition to shape, the lengths of first section 30 and second section 32 may also vary. For example, the shape of loop 20 may be generally circular and first section 30 and second section 32 may each span any proportion of the circumference of loop 20. The same observation may be true for other loop 20 shapes (which include any appropriate shape). Additionally, the transition between first section 30 and second section 32 may vary so as to be generally gradual, abrupt, or in any suitable manner.

It can be seen in FIG. 3 that in at least some embodiments, filter loop 20 and struts 22 may be continuous with one another and may be defined by a uninterrupted wire or fiber 34. According to these embodiments, fiber 34 may include a proximal end 36, a first strut region 38, a filter loop region 40 defining filter loop 20 (including first section 30 and second section 32), a second strut region 42, and a distal end 44. Proximal end 36 and distal end 44 of fiber 34 may be coupled to cartridge 16, for example by helically winding them about cartridge 16 or by any other suitable method including those described herein. A bond or coupling 46 may be disposed at the junctions of strut regions 38/42 and filter loop region 40. The form of bond 46 may vary and could be a solder or other type of joint, weld, mechanical connection, and the like, or any other suitable type of coupling.

Fiber 34 can be defined by a solid shaft, a tubular shaft, a shaft defined by a plurality of mirco-filaments, and the like. Fiber 34 may be manufactured from any appropriate material including any of those described herein. For example, fiber 34 may include a metal alloy such as nickel-titanium alloy. Although some embodiments include fiber 34 that is continuous so as to define the structures listed above, this need not be the case. For example, struts 22 and filter loop 20 (as well as any of the other structures) may be formed from distinct structures that are attached by essentially any suitable means.

Because some embodiments of filter loop 20 include fiber 34, first section 30 may be split into two sections (indicated in FIG. 3 as sections 30a and 30b) that are on opposite sites of the junction of filter loop 20 and struts 22 (e.g., adjacent bond 46). It can be appreciated, however, that the positioning and configuration of first section 30 may vary from simply being spit adjacent bond 46. For example, first section 30 and second section 32 may be on opposite sides of the bond 46. Any other suitable configuration or positioning may be substituted without departing from the spirit of the invention.

Figure 4:
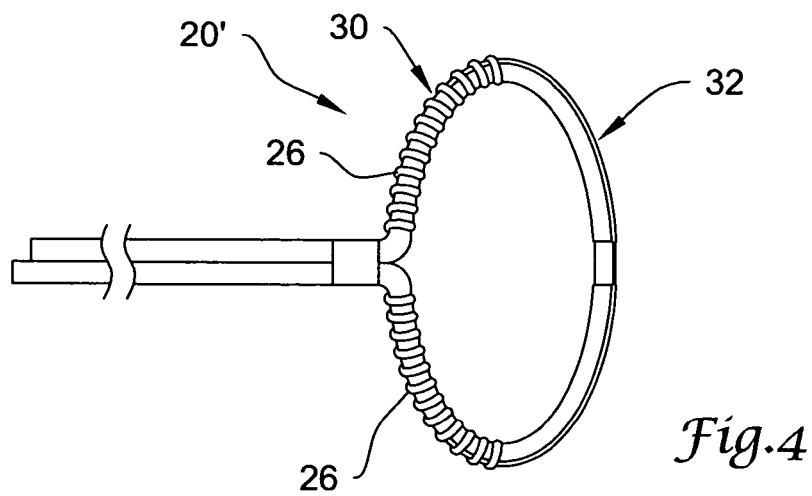
FIG. 4 is a plan view of another example filter loop.

As stated above, coil 26 may be disposed over a portion of filter loop 20. For example, coil 26 may be disposed over first section 30 of filter loop 20. In some embodiments, for example embodiments where first section 30 is split into sections 30a/b, a plurality of coils 26 (for example two coils 26 as shown in FIG. 3) may be disposed about sections 30a/b. Alternatively, coil 26 may be disposed over only one of sections 30a/b, over second section 32, over portions of both first and second sections 30/32, or at any suitable position. For example, FIG. 4 illustrates an example loop 20' where coil 26 is disposed over a portion of first section 30 and second section 32. Coil 26 may also have a number of differing forms or configurations. For example, coil 26 may vary in length, cross-sectional thickness, material composition, position, etc. In some interventions coil 26 may not be necessary so that coil 26 can be omitted or can be removed from loop 20' (or any other loop described herein).

Also as stated above, filter loop 20 may include loop tip 28. In some embodiments, loop tip 28 is disposed adjacent second section 32. For example, loop tip 28 may be defined along a portion or along the entire length of second section 32. Loop tip 28, in general, may be more amenable to folding than other portions of filter loop 20. For example, loop tip 28 may be defined by a thinned region of second section 32. Alternatively, loop tip 28 may be defined in other ways such as mechanical or shape alterations, material differences, or in any other appropriate way. The exact position and/or length of loop tip 28 may vary so as to be at essentially any position along filter loop 20 and to span any suitable length. Additionally, filter loop 20 may include additional loop tips similar to tip 28. This may allow filter 14, for example, to have a plurality of pre-defined folding points or positions.

By pre-defining a folding position along loop 20, for example at loop tip 28, it may be easier to dispose and/or remove filter 14 from a delivery or retrieval device. This may be because less force may be required to collapse or otherwise fold filter 14 (i.e., at loop tip 28) to a lower profile. Moreover, pre-defined folding positions may be selectively positioned in order to optimize the folded profile of filter 14 for differing uses. For example, positioning of loop tip or tips 28 may allow filter 14 to be collapsed to relatively low profiles so as to be useable at small or sensitive intravascular locations such as those near the brain.

Figure 5:
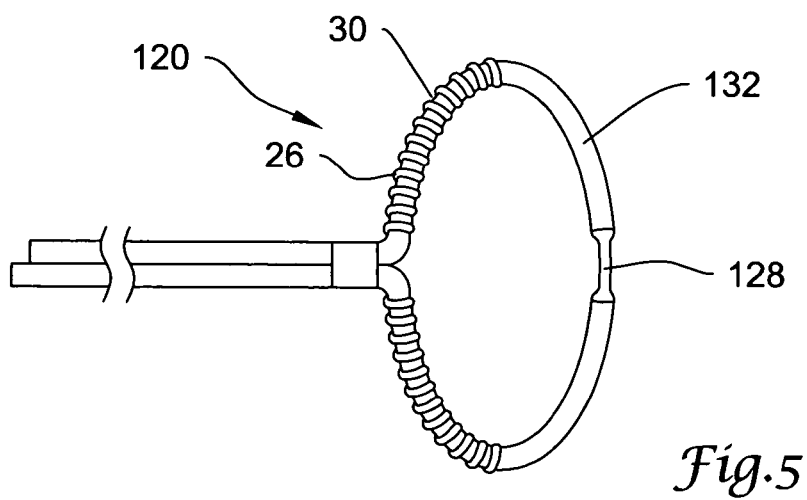
FIG. 5 is a plan view of another example filter loop.

Another example filter loop 120 is shown in FIG. 5. Loop 120 is similar to loop 20 except that second section 132 is thinned relative to first section 30. Thus, FIG. 3 illustrates that the shape of the loop tips disclosed herein may vary. For example, loop tip 28 is generally depicted in FIGS. 1-4 as being rectangular in cross-sectional shape. However, this need not be the case. For example, loop tip 128 is shown as having a round cross-sectional shape. It can be appreciated that any other suitable shape may be used without departing from the sprit of the invention. For example, loop tip 128 could have a cross-sectional shape that is triangular, square, polygonal, irregular, and the like.

In some embodiments, first section 30 and second section 132 may both be generally rounded and include a generally circular cross-sectional shape. Thus, loop tip 128 may be defined as a thinned and rounded region of second section 132. Alternatively, second section 132 may be thinned and have a shape that differs from first section 30. For example, second section 132 may be flattened similar to what is describe above in relation to FIGS. 3 and 4.

The transition between first section 30 and second section 132 may vary. For example, some embodiments may include a gradual taper in outside diameter that may be formed using known grinding techniques. Alternatively, the transition may be somewhat more abrupt. This later embodiment may allow second section 132 (or a portion thereof) to define loop tip 128. In still other embodiments, multiple thinned sections may be defined along second section 132. For example, second section 132 may include alternating thinning and thickening regions. It can be appreciated that the thinning regions may define one or more loop tips (similar to loop tip 128).

Figure 6:
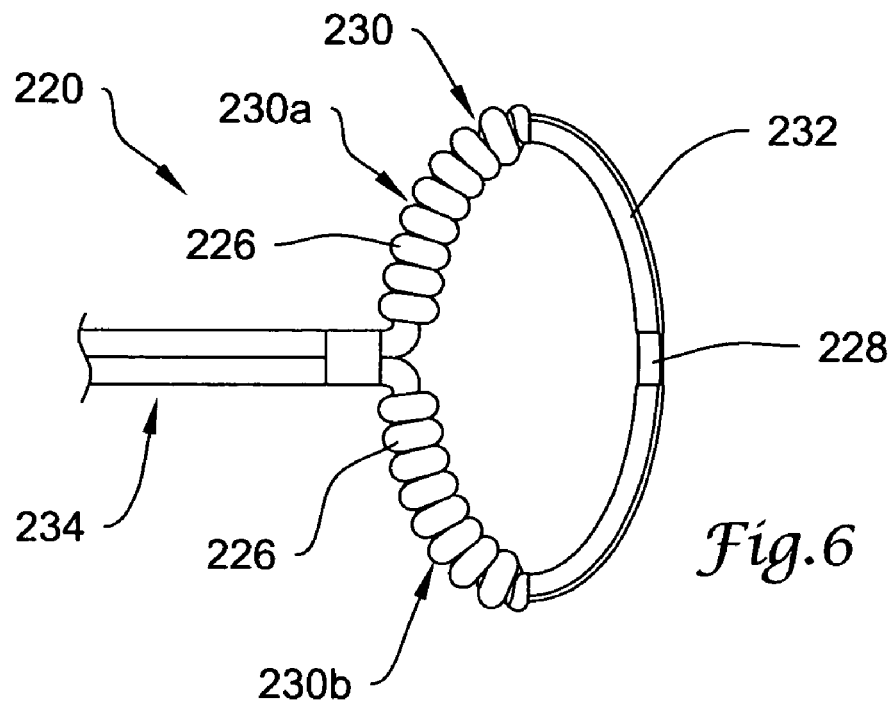
FIG. 6 is a plan view of another example filter loop.

FIG. 6 illustrates another example filter loop 220. Loop 220 is similar to other loops described herein except that coil 226 is defined by helical winding in shaft 234. According to this embodiment, loop 220 may include coiled regions that define coil 226, for example adjacent first section 230. Moreover, because first section 230 may include multiple regions, for example first section 230a and first section 230b, loop 220 may also include multiple coiled regions or coils 226. Filter loop 220 may also include second section 232 that may be flattened, thinned, or both as described above. Additionally, loop may include loop tip 228, for example adjacent second section 232.

Figure 7:
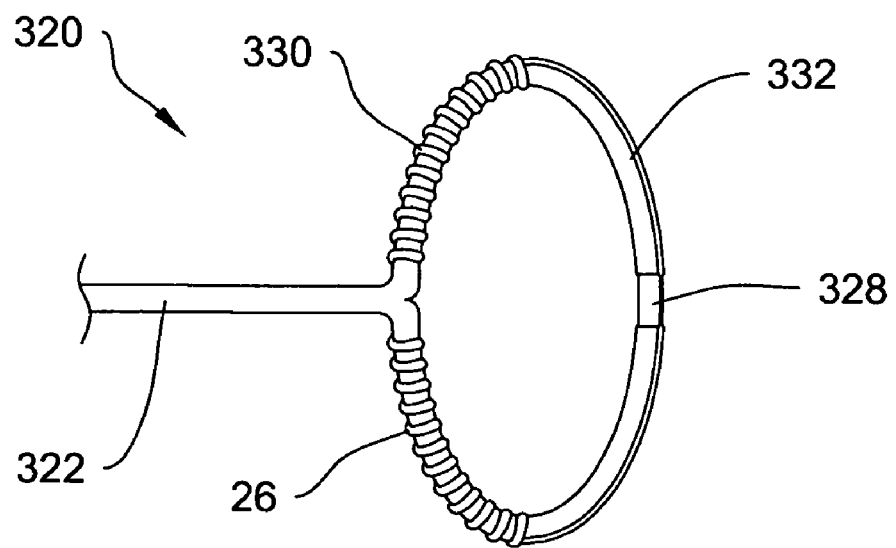
FIG. 7 is a plan view of another example filter loop.

FIG. 7 illustrates another example filter loop 320. Loop 320 is similar to other loops described herein except that loop 320 may be defined by a fork 348 in strut 322. According to this embodiment, loop 320 can be formed from splitting one end of strut 322 and forming the split end into a loop. Loop 320 may include first section 330, second section 332, and loop tip 328, which may be similar to the analogous structures above. For example, coil 26 (or a plurality of coils 26) may be disposed adjacent first section 330. Additionally, second section 332 may be at least partially flattened and/or thinned, and may include loop tip 328.

In some embodiments, loop tip 328 may be defined at the position where the opposite ends of split strut 322 are joined to define loop 320. According to this embodiment, the coupling of the strut ends may be carried out in a manner that may make loop tip 328 more amenable to folding. For example, a thinned mechanical fitting may be disposed adjacent the strut 322 end to define loop tip 328.

Figure 8:
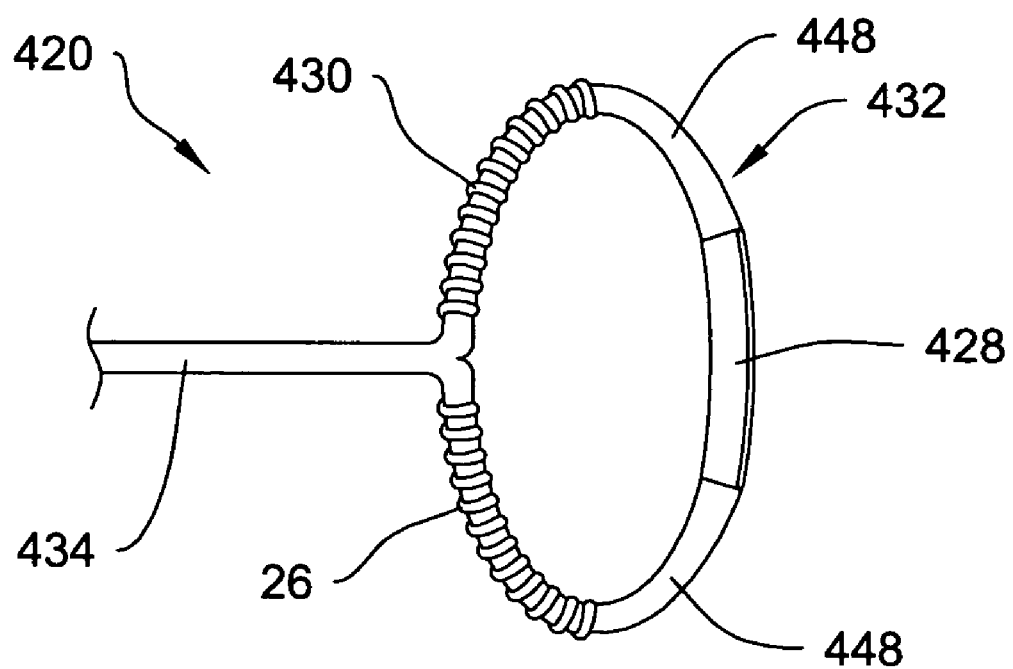
FIG. 8 is a plan view of another example filter loop.

Another example filter loop 420 is shown in FIG. 8. Loop 420 is similar to the other devices described herein except that second section 432 includes one or more transition regions 448 disposed adjacent loop tip 428. In general, transition regions 448 are regions of loop 420 transitions in shape. For example, first section 430 may have a generally circular cross-sectional shape that transitions to the generally rectangular cross-sectional shape of loop tip 428. It can be seen in FIG. 8 that the shape of loop tip 428 may be wider and thinner than other portions of loop 420. Therefore, in addition to changing from being circular in cross-sectional shape to being rectangular in cross-sectional shape, transition regions 448 may also change loop 420 from being relatively narrow and thick (e.g., adjacent first section 430) to being thin and wide (e.g., adjacent loop tip 428).

The position of transition regions 448 may vary. For example, transition regions 448 may be disposed at the junction of first section 430 and second section 432 (i.e., at the end of coils 26). However, transition regions 448 may be disposed at other locations including partially under coils 26 (i.e., similar to the position of second section 32 as shown in FIG. 4), a distance away from coils 26, or at any other suitable location. The shape of transition regions 448 may also vary and can change in a regular or proportional fashion, in an irregular or non-proportional manner, in a step-wise fashion, in a random fashion, and the like, or in any other suitable manner.

The transition from first section 430, through transition regions 448, and to loop tip 428 can be defined in any one of a number of suitable manners or manufacturing techniques. For example, it may be desirable to stamp, coin, or machine the rectangular, thin, and wide loop tip 428. It can be appreciated, however, that any other suitable manufacturing methods may be used without departing from the sprit of the invention.

Manufacturing of devices that include any of the structures described herein may include disposing the filter loop on an appropriate forming member or mandrel. This step may include bending the filter loop into the desired shape, flattening or otherwise varying a portion of the filter loop, disposing coil 26 adjacent the filter loop, etc. Filter membrane 24 may be coupled to the filter loop in an appropriate manner. For example, filter membrane 24 may be coupled to the filter loop by dip molding the forming member (including the filter loop), spray molding, or any other appropriate means.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering device, comprising:
   a shaft;
   one or more struts coupled to the shaft;
   a filter loop coupled to the one or more struts, the filter loop including a first section having a generally circular cross-section and a second flattened ribbon section, the second flattened ribbon section including a thinned region; and
   a filter membrane coupled to the filter loop and extending distally therefrom; wherein the ribbon section is disposed opposite the shaft.

2. The filtering device of claim 1, wherein the shaft includes a guidewire.

3. The filtering device of claim 1, wherein the shaft includes a tubular filter cartridge.

4. The filtering device of claim 1, further comprising a coil disposed about a portion of the filter loop.

5. The filtering device of claim 4, wherein the coil includes a radiopaque material.

6. The filtering device of claim 1, wherein a coil is disposed on the generally circular first section.

7. The filtering device of claim 1, wherein the one or more struts are continuous with the filter loop.

8. A medical device, comprising:
   a tubular filter cartridge;
   a fiber defining a strut and filter loop assembly, the fiber including a proximal end, a first strut section, a filter loop section, a second strut section, and a distal end;
   wherein the proximal end and the distal end of the fiber are coupled to the filter cartridge;
   wherein the filter loop section includes a coil region, a section having a generally circular cross-section, and a flattened region, the flattened region further having a thinned section; a filter membrane coupled to the filter loop section; and wherein further comprising a loop tip disposed adjacent the flattened region.

9. The medical device of claim 8, wherein the coil region is defined by a coil disposed about a portion of the filter loop section.

10. The medical device of claim 9, wherein the coil includes a radiopaque material.

11. The medical device of claim 8, wherein the loop tip is defined by the thinned section of the flattened region.

12. An embolic protection filtering device, comprising:
a shaft;
a filter loop and strut assembly coupled to the shaft, the assembly including a strut region and a filter loop region;
the strut region including one or more struts;
the filter loop region including a section of generally circular cross-section and a section of generally squared or rectangular cross-section;
wherein the generally rectangular cross-section includes a loop tip;
a radiopaque coil disposed about the section of generally circular cross-section; and
a filter membrane coupled to the filter loop region;
wherein the loop tip is defined by a thinned section of the filter loop region.

13. The filtering device of claim 12, wherein the shaft includes a guidewire.

14. The filtering device of claim 12, wherein the shaft includes a tubular filter cartridge.

15. A medical device, comprising:
a tubular filter cartridge;
one or more struts disposed about the filter cartridge;
a filter loop including a first section having a generally circular cross-section and a second section having a generally flattened loop tip with a generally rectangular cross-section; and wherein the loop tip is defined by a thinned section of the filter loop;
a filter membrane coupled to the filter loop;
the one or more struts extending between the filter loop and the filter cartridge; and
means for visualizing the filter loop.

* * * * *